(12) United States Patent
Nichols et al.

(10) Patent No.: US 8,897,630 B2
(45) Date of Patent: Nov. 25, 2014

(54) PULSED AEROSOL GENERATION

(71) Applicant: Philip Morris USA Inc., Richmond, VA (US)

(72) Inventors: Walter A. Nichols, Chesterfield, VA (US); David Keeler, Midlothian, VA (US); Christopher Tucker, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 13/891,810

(22) Filed: May 10, 2013

(65) Prior Publication Data

US 2013/0243410 A1    Sep. 19, 2013

Related U.S. Application Data

(63) Continuation of application No. 12/230,415, filed on Aug. 28, 2008, now Pat. No. 8,442,390.

(60) Provisional application No. 60/935,749, filed on Aug. 29, 2007.

(51) Int. Cl.
| A61H 33/12 | (2006.01) |
| F24F 6/08 | (2006.01) |
| A61L 9/03 | (2006.01) |
| A61L 9/14 | (2006.01) |
| F24F 6/02 | (2006.01) |
| F24F 3/16 | (2006.01) |

(52) U.S. Cl.
CPC .......... *A61L 9/037* (2013.01); *F24F 2003/1689* (2013.01); *A61L 9/14* (2013.01); *F24F 6/025* (2013.01)
USPC ............ 392/403; 392/395; 392/397; 392/405

(58) Field of Classification Search
None
See application file for complete search history.

(56) References Cited

U.S. PATENT DOCUMENTS

| 4,020,321 A | 4/1977 | Oswald |
| 4,676,237 A | 6/1987 | Wood et al. |
| 4,740,366 A | 4/1988 | Winston et al. |
| 5,011,632 A | 4/1991 | Yano et al. |
| 5,095,647 A | 3/1992 | Zobele et al. |
| 5,196,171 A | 3/1993 | Peltier |
| 5,221,025 A | 6/1993 | Privas |
| 5,290,546 A | 3/1994 | Hasegawa et al. |

(Continued)

FOREIGN PATENT DOCUMENTS

| EP | 0897755 A2 | 2/1999 |
| EP | 1762253 A2 | 3/2007 |
| WO | WO 2006/105154 A2 | 10/2006 |

OTHER PUBLICATIONS

U.S. Appl. No. 61/251,186, filed Oct. 13, 2009.

(Continued)

*Primary Examiner* — Thor Campbell
(74) *Attorney, Agent, or Firm* — Buchanan Ingersoll & Rooney PC

(57) ABSTRACT

An aerosol generator periodically forms aerosolized fragrance material by repeatedly supplying a liquid fragrance material to a capillary passage via only capillary action and heating the capillary passage, such that the liquid fragrance material at least partially volatilizes and is driven out of an outlet of the capillary passage. A wick feeds the liquid fragrance material to an inlet of the capillary passage by capillary action. An apparatus and method for generating such an aerosolized fragrance material, as well as the methods of heating, are disclosed.

14 Claims, 4 Drawing Sheets

(56) References Cited

U.S. PATENT DOCUMENTS

| | | |
|---|---|---|
| 5,382,410 A | 1/1995 | Peltier |
| 5,484,086 A | 1/1996 | Pu |
| 5,591,409 A | 1/1997 | Watkins |
| 5,647,053 A | 7/1997 | Schroeder et al. |
| 5,743,251 A | 4/1998 | Howell et al. |
| 5,972,290 A | 10/1999 | De Sousa |
| 6,155,268 A | 12/2000 | Takeuchi |
| 6,236,807 B1 | 5/2001 | Ruffolo et al. |
| 6,238,646 B1 | 5/2001 | Zembrodt |
| 6,293,474 B1 | 9/2001 | Helf et al. |
| 6,296,196 B1 | 10/2001 | Denen et al. |
| 6,325,475 B1 | 12/2001 | Hayes et al. |
| 6,361,752 B1 | 3/2002 | Demarest et al. |
| 6,378,780 B1 | 4/2002 | Martens, III et al. |
| 6,386,462 B1 | 5/2002 | Martens, III |
| 6,412,494 B1 | 7/2002 | Bloom, Jr. |
| 6,439,474 B2 | 8/2002 | Denen |
| 6,491,233 B2 | 12/2002 | Nichols |
| 6,495,097 B1 | 12/2002 | Streit et al. |
| 6,501,052 B2 | 12/2002 | Cox et al. |
| 6,516,796 B1 | 2/2003 | Cox et al. |
| 6,536,746 B2 | 3/2003 | Watkins |
| 6,557,552 B1 | 5/2003 | Cox et al. |
| 6,568,390 B2 | 5/2003 | Nichols et al. |
| 6,602,475 B1 | 8/2003 | Chiao |
| 6,640,050 B2 | 10/2003 | Nichols et al. |
| 6,661,967 B2 | 12/2003 | Levine et al. |
| 6,666,909 B1 | 12/2003 | TeGrotenhuis et al. |
| 6,681,769 B2 | 1/2004 | Sprinkel, Jr. et al. |
| 6,681,998 B2 | 1/2004 | Sharpe et al. |
| 6,697,571 B2 | 2/2004 | Triplett et al. |
| 6,701,921 B2 | 3/2004 | Sprinkel, Jr. et al. |
| 6,701,922 B2 | 3/2004 | Hindle et al. |
| 6,715,487 B2 | 4/2004 | Nichols et al. |
| 6,752,327 B2 | 6/2004 | Martens, III et al. |
| 6,766,220 B2 | 7/2004 | McRae et al. |
| 6,772,757 B2 | 8/2004 | Sprinkel, Jr. |
| 6,786,427 B2 | 9/2004 | Schram et al. |
| 6,789,741 B2 | 9/2004 | Varanasi et al. |
| 6,792,199 B2 | 9/2004 | Levine et al. |
| 6,793,149 B2 | 9/2004 | Schramm et al. |
| 6,799,572 B2 | 10/2004 | Nichols et al. |
| 6,804,458 B2 | 10/2004 | Sherwood et al. |
| 6,843,430 B2 | 1/2005 | Boticki et al. |
| 6,854,470 B1 | 2/2005 | Pu |
| 6,871,792 B2 | 3/2005 | Pellizzari |
| 6,883,516 B2 | 4/2005 | Hindle et al. |
| 6,899,280 B2 | 5/2005 | Kotary et al. |
| 6,909,840 B2 | 6/2005 | Harwig et al. |
| 6,923,179 B2 | 8/2005 | Gupta et al. |
| 6,994,843 B2 | 2/2006 | Rabinowitz et al. |
| 7,040,314 B2 | 5/2006 | Nguyen et al. |
| 7,090,830 B2 | 8/2006 | Hale et al. |
| 7,100,841 B2 | 9/2006 | Ivey et al. |
| 7,117,867 B2 | 10/2006 | Cox et al. |
| 7,147,170 B2 | 12/2006 | Nguyen et al. |
| 7,167,641 B2 | 1/2007 | Tam et al. |
| 7,173,222 B2 | 2/2007 | Cox et al. |
| 7,367,334 B2 | 5/2008 | Faison, Jr. et al. |
| 7,400,940 B2 | 7/2008 | McRae et al. |
| 7,500,479 B2 | 3/2009 | Nichols et al. |
| 7,683,029 B2 | 3/2010 | Hindle et al. |
| 7,743,766 B2 | 6/2010 | Gupta et al. |
| 7,798,420 B2 | 9/2010 | Lind et al. |
| 8,201,752 B2 | 6/2012 | Brodbeck et al. |
| 8,414,522 B2 | 4/2013 | Kamen et al. |
| 8,442,390 B2 | 5/2013 | Nichols et al. |
| 2004/0265164 A1 | 12/2004 | Woo et al. |
| 2008/0251598 A1 | 10/2008 | Ross |
| 2009/0230117 A1 | 9/2009 | Fernando et al. |
| 2011/0253798 A1 | 10/2011 | Tucker et al. |

OTHER PUBLICATIONS

U.S. Appl. No. 12/791,407, filed Jun. 1, 2010 (now abandoned).

Utada, A. S. et al., "Monodisperse Double Emulsions Generated from a Microcapillary Device", Science (vol. 38), Apr. 22, 2005, pp. 537-541.

International Search Report and Written Opinion mailed May 28, 2009 for PCT/IB2008/003020.

International Preliminary Report on Patentability mailed Mar. 11, 2010 for PCT/IB2008/003020.

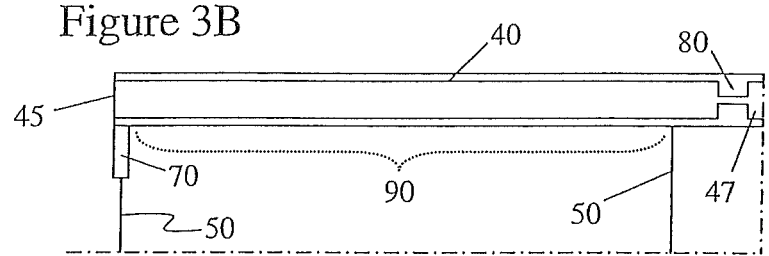
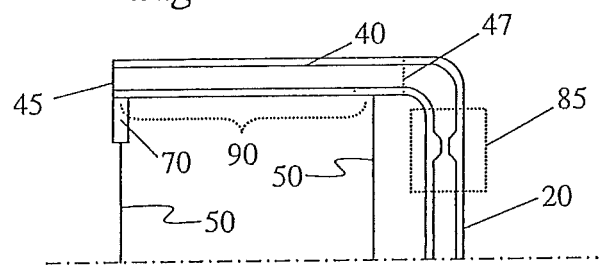

PULSED AEROSOL GENERATION

CROSS-REFERENCE TO RELATED APPLICATIONS

This application claims priority under 35 U.S.C. §119(e) to U.S. provisional Application No. 60/935,749, filed Aug. 29, 2007, the entire content of which is incorporated herein by reference.

SUMMARY

Provided is an air freshener for generation of aerosolized liquid fragrance material comprising a capillary passage having an inlet and an outlet; a liquid supply operable to supply liquid fragrance material to the inlet of the capillary passage only via capillary action; and a power supply adapted to apply voltage across a heater arranged along the capillary passage to heat liquid fragrance material in the capillary passage to a temperature sufficient to at least partially volatilize liquid fragrance material in the capillary passage such that the liquid fragrance material is driven out of the outlet of the capillary passage and forms an aerosol of the liquid fragrance material.

Additionally provided is a method for pulsed generation of aerosolized fragrance material comprising drawing liquid fragrance material into a capillary passage having an inlet and an outlet only via capillary action and periodically applying voltage across a heater arranged along the capillary passage to heat liquid fragrance material in the capillary passage to a temperature sufficient to at least partially volatilize the liquid fragrance material such that the fragrance material is driven out of the outlet of the capillary passage and forms an aerosol of the fragrance material.

In another embodiment a method of producing an aerosol of liquid is provided. The method includes disposing a liquid along a zone of a capillary passage by drawing a liquid via capillary action from a liquid supply into said zone; repetitively applying heat according to a power cycle along at least a portion of said zone, the heat of each power cycle being sufficient to volatilize substantially all said disposed liquid along said zone so that during said power cycle, said drawing of liquid via capillary action is interrupted and that at conclusion of each power cycle, said disposed liquid along said zone is evacuated from said heated zone; and spacing said power cycles sufficiently apart in time for said drawing liquid via capillary action to resume and refill said zone between power cycles.

In still another embodiment, an aerosol generator to generate an aerosolized liquid material is provided. The aerosol generator comprises a capillary passage having an inlet, an outlet and a zone along the capillary passage between the inlet and outlet, the zone operable to be heated; a liquid supply to supply a liquid material to the inlet of the capillary passage to be drawn into the zone of the capillary passage via capillary action; and a power supply operable to repetitively apply heat according to a power cycle along at least a portion of the zone of the capillary passage to volatilize the liquid material disposed in the heated zone so that during the power cycle, the drawing of liquid via capillary action is interrupted and that at conclusion of each power cycle, the disposed liquid along the zone is evacuated from the heated zone, the power cycles sufficiently spaced apart in time for drawing liquid via capillary action to resume and refill the zone between power cycles.

BRIEF DESCRIPTION OF THE DRAWINGS

FIGS. 3A-3C show another exemplary embodiment of the air freshener and exemplary embodiments of a capillary passage used therein.

DETAILED DESCRIPTION OF PREFERRED EMBODIMENTS

Figure 1:
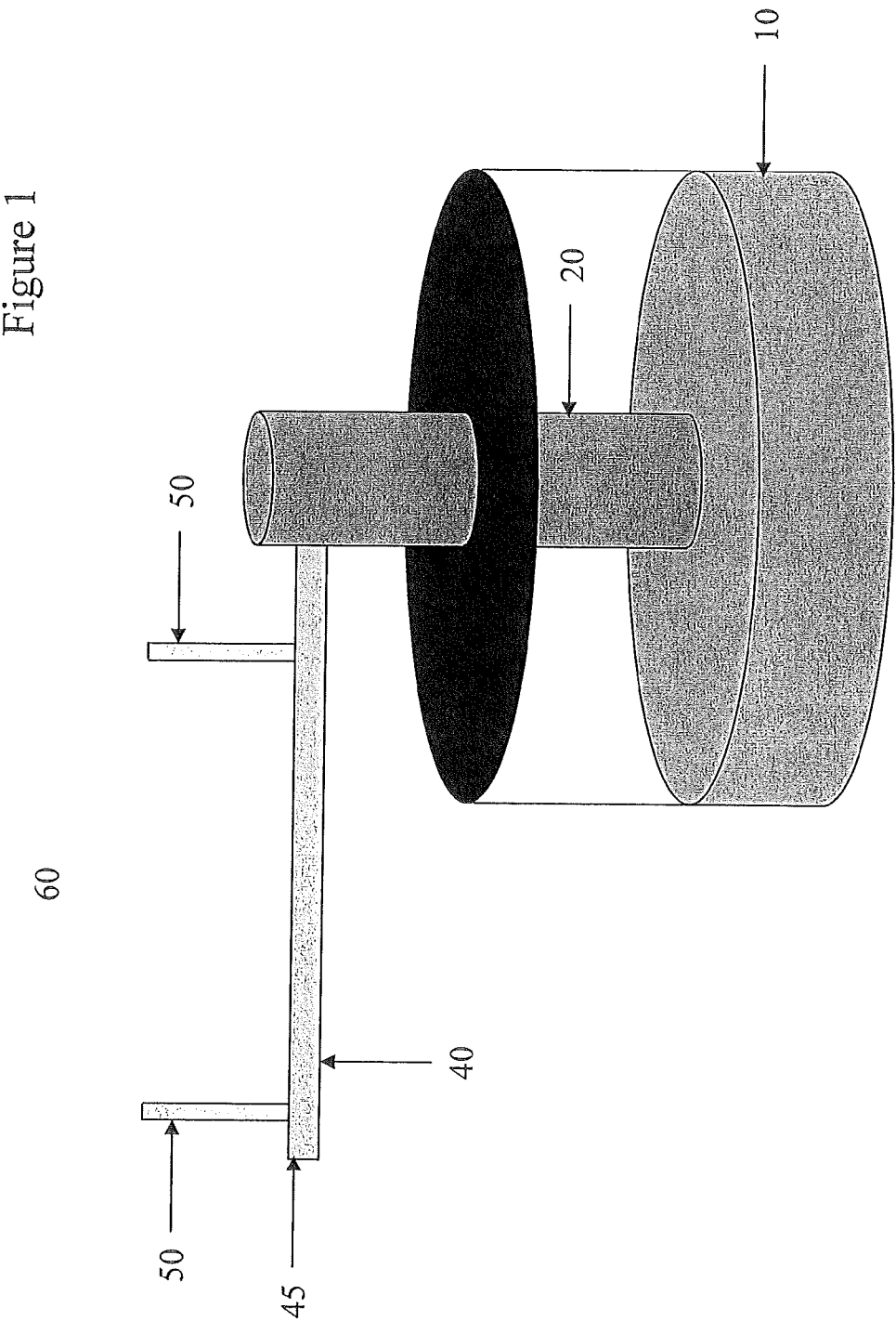
FIG. 1 is a representation of an exemplary embodiment of the air freshener.

Provided is an air freshener for generation of aerosolized fragrance material, which is admixed with ambient air. The air freshener includes a capillary passage having an inlet and an outlet; a liquid supply operable to supply liquid fragrance material to the inlet of the capillary passage only via capillary action; and a power supply adapted to apply voltage across a heater arranged along the capillary passage to heat liquid fragrance material in the capillary passage to a temperature sufficient to at least partially volatilize liquid fragrance material in the capillary passage, such that the fragrance material is driven out of the outlet of the capillary passage and mixes with the ambient air to form an aerosol.

Preferably, the capillary passage has an internal diameter of 0.01 to 10 mm, preferably 0.05 to 1 mm, more preferably 0.05 to 0.4 mm, and even more preferably about 0.05 mm. Alternatively, the capillary passage preferably has an internal cross sectional area of $8 \times 10^{-5}$ to 80 $mm^2$, preferably 0.002 to 0.8 $mm^2$, more preferably 0.002 to 0.05 $mm^2$, and even more preferably about 0.002 $mm^2$. The capillary passage may optionally have a reduced diameter, or a restricted orifice, at the outlet of the capillary passage. For example, for a capillary passage having an internal diameter of about 0.15 mm, the restricted orifice at the outlet may have an internal diameter of about 0.05 mm.

While not wishing to be held to any particular theory, it is believed that a reduced diameter (restricted orifice) at the outlet of the capillary passage produces aerosol by a fluid shearing mechanism, in which coarse droplets of liquid fragrance material in the capillary passage are broken up into smaller ones, as a result of high pressure created in the capillary passage by heating and at least partial volatilization of the liquid fragrance material, which provides a driving force to expel liquid and/or volatilized fragrance material out of the outlet of the capillary passage. Thus, liquid fragrance material may be aerosolized by passing through a reduced diameter outlet of the capillary passage as heating the liquid fragrance material creates pressure in the capillary passage, which expels the liquid fragrance material out of the outlet of the capillary passage.

In most applications, however, the capillary passage preferably comprises a "straight tube" configuration not having a constricted tip.

The capillary passage may have a length of about 10 to 40 mm, e.g., about 25 mm. The capillary passage preferably is the interior of a stainless steel capillary tube, such as, for example, 304 stainless steel, which serves as a heater via electrical leads attached thereto for passage of direct or alternating current along a length of the tube. Thus, the stainless steel tube is heated by resistance heating. The stainless steel tube is preferably circular in cross section. The tube may be a hypodermic needle of various gauges. For example, a 32 gauge needle has an internal diameter of 0.11 mm and a 26 gauge needle has an internal diameter of 0.26 mm.

However, the capillary tube may be any electrically conductive material capable of being resistively heated, while retaining the necessary structural integrity at the operating temperature experienced by the capillary passage, and which is sufficiently non-reactive with the liquid fragrance material.

Such materials include, but are not limited to stainless steel, INCONEL, metal composites, or other metals and alloys.

In an additional embodiment, the capillary passage may be the interior of a non-metallic tube such as, for example, a glass tube. In such an embodiment, the heater, an electrically conductive material capable of being resistively heated, such as, for example, stainless steel, NICHROME or platinum wire, is arranged along the glass tube. When the heater arranged along the glass tube is heated, liquid fragrance material in the capillary passage is heated to a temperature sufficient to at least partially volatilize liquid fragrance material in the capillary passage. Electrical leads may connect the heater to a power supply.

The power supply for applying a voltage may include a voltage source and two electrical leads. The voltage source can be a direct current battery. However, the use of alternating current could also be effective. In the use where the capillary passage is the interior of a stainless steel tube, the electrical leads are preferably attached to spaced apart locations along the tube to supply power that resistively heats the tube.

The power supply preferably delivers a pulse of power to the capillary heater via the electrical leads. The voltage chosen determines the amount of energy that will be used to heat the capillary passage in each pulse. The energy transferred to the capillary passage from the voltage source is governed by Ohm's Law.

$$V(\text{voltage}) = I(\text{current}) \cdot R(\text{resistance}) \quad (1)$$

$$\text{Power} = V \cdot I = V^2/R \quad (2)$$

Preferably, the liquid supply is vented. The liquid supply may include a wick that delivers liquid fragrance material from the liquid supply to the inlet of the capillary passage only via capillary action. Preferably, the wick material contains numerous pores, and these pores act as capillary passages, which cause the liquid fragrance material to be drawn into them and then into an inlet of the capillary passage.

While the wick can be made of a variety of materials, porous plastic wicks are preferred. An example of a porous plastic wick is a wick composed of ultra high molecular weight, high density polyethylene (HDPE). Such wicks are generally made of blends of HDPE in particle form, and the blends are developed to meet the target pore characteristics of the wick. Preferably, the solubility parameter of the polymer is significantly different from that of the liquid fragrance material, which prevents the wick from swelling or other changes that can lead to a change in the pore size and porosity of the wick.

The liquid fragrance material may be any suitable liquid fragrance material that can be delivered to the capillary passage for generation of aerosolized fragrance material. For example, the liquid fragrance material may be any commercially available liquid fragrance material suitable for use in commercial air fresheners. The liquid fragrance material is preferably aqueous based, alcohol based, such as, for example, methanol, or propylene glycol based.

Manipulation of parameters of the air freshener, such as, for example, the internal diameter of the capillary passage and/or heat transfer characteristics of the material defining the capillary passage, can be selected to control heater temperature and mass median particle diameter. Furthermore, choice of the liquid fragrance material can affect heater temperature and mass median particle diameter of the aerosolized material.

Additionally provided is a method for generation of aerosolized fragrance material, which includes drawing liquid fragrance material into an inlet of a capillary passage only via capillary action and periodically applying voltage across a heater arranged along the capillary passage to heat liquid fragrance material in the capillary passage to a temperature sufficient to at least partially volatilize the liquid fragrance material, such that fragrance material is driven out of an outlet of the capillary passage.

After the voltage is applied across a heater arranged along the capillary passage and the fragrance material is driven out of the outlet of the capillary passage, the capillary passage cools and is again refilled only via capillary action. The capillary passage refill time is a function of the length and diameter of the capillary passage as well as the properties of the wick and liquid fragrance material. For example, for a 25 mm long, 0.15 mm internal diameter capillary passage, refill can occur in less than 10 seconds. Thus, after the capillary passage cools and draws in more liquid fragrance material, the heater is again activated by control circuitry effective to periodically apply voltage across a heater arranged along the capillary passage to heat liquid fragrance material in the capillary passage to a temperature sufficient to at least partially volatilize the liquid fragrance material such that fragrance material is driven out of the outlet of the capillary passage. Accordingly, a method for repeated pulsed generation of aerosolized fragrance material includes aerosolizing fragrance material, cooling the capillary passage, and repeating the filling and aerosolization steps.

The frequency of repeated pulsed generation of aerosolized fragrance material is limited by the capillary passage refill time. Thus, depending on the length and diameter of the capillary passage and the liquid fragrance material, aerosolized fragrance material may be generated as frequently as every 2 to 100 seconds, perhaps at least once a minute, or less frequently, such as, for example, at least once an hour or at least once a day. In order for the capillary passage to be effectively refilled only via capillary action, substantially all of the liquid fragrance material contained in the capillary passage is driven out of the capillary passage, thus providing a substantially dry capillary passage.

The air freshener may be implemented in a small device, with the power supply being a battery. Alternatively, the power supply may be an alternating current (AC) source, such as an AC outlet and the air freshener can include a converter if desired to convert the AC to direct current supplied to the heater. The air freshener may be operated by control circuitry operable to deliver power from the power supply to the heater in timed heating cycles such that the liquid fragrance material is at least partially volatilized after capillary leading of the capillary passage. Thus, the control circuitry controls the application of voltage across the heater in order to aerosolize the fragrance material. Specifically, the control circuitry may control the frequency of application of voltage across the heater in order to aerosolize the fragrance material. The control circuitry may automatically control the frequency of repeated pulsed aerosolization of fragrance material. Alternatively, the frequency of repeated pulsed generation of aerosolized fragrance material may be preset or manually set, with the control circuitry controlling generation of aerosolized fragrance material according to the preset or manually selected frequency. If desired, the control circuitry/power supply may include primary and/or secondary cells, preferably primary cells, capacitors including supercapacitors, charge pumps, and combinations thereof. Use of a supercapacitor may extend battery life and/or allow for use of fewer or smaller batteries.

FIG. 1 is a representation of an exemplary embodiment of the air freshener. A liquid supply 10 supplies liquid fragrance material to a wick 20, which supplies the liquid fragrance material to an inlet of a capillary tube 40 preferably of stainless steel and having an outlet 45. Attached to the capillary tube 40 are electrical leads 50 for supplying voltage to the capillary tube 40. The electrical leads 50 are connected to control circuitry 60, which regulates the power supplied to the capillary tube 40. Pulsed delivery of power to the capillary tube 40 causes volatilized liquid fragrance material to periodically be driven out of the outlet 45 of the capillary tube 40 and form an aerosol.

Figure 2:
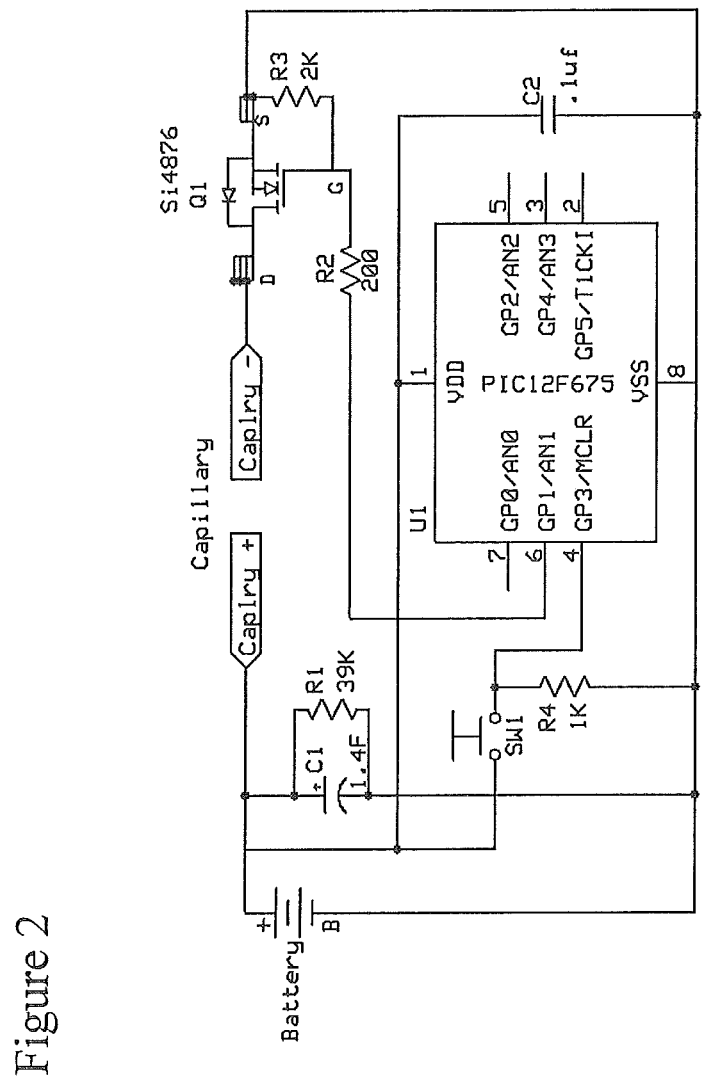
FIG. 2 is a schematic of exemplary control circuitry.

FIG. 2 is a schematic of exemplary control circuitry, including a heater for the capillary tube ("capillary" in FIG. 2) and electrical leads ("Caplry+" and "Caplry−"). These leads can be attached at spaced apart locations along a stainless steel capillary tube in which liquid fragrance material is heated by pulsing power through the leads. While the control circuitry may be powered by one or more batteries, such as AA cells, the control circuitry of FIG. 2 is powered by one battery B. The control circuitry preferably comprises a master power switch SW1, as well as a microcontroller U1, such as a PIC12F675, manufactured by Microchip. The microcontroller U1 illustrated in FIG. 2 has unutilized outputs 2, 3, 5, 7, which may be employed depending on the complexity of the control circuitry. The timing of energizing the heater of the air freshener is preferably set by an internal clock of the microcontroller. For adjustable timing, a pushbutton switch can be pressed one or more times to set the time interval between aerosol delivery. An indicator LED displaying information such as the set time interval may also be controlled by the microcontroller. The field effect transistor Q1, such as, for example, Si4876, is used to switch power to the capillary heater under control of the microcontroller. While energy can be directly delivered to the heater by the battery, the control circuitry of FIG. 2 has a power supply that includes a supercapacitor C1, which supplies energy as an energy pulse to the capillary heater, i.e., the supercapacitor discharges a pulse of energy to the heater sufficient to aerosolize the liquid fragrance material in the capillary passage. The microcontroller U1 is preprogrammed or manually set for a timing cycle whose duration is shorter than time required for the supercapacitor C1 to recharge. Additional elements of the control circuitry illustrated in FIG. 2 include a capacitor C2 and resistors R1, R2, R3, R4.

Figure 3A:
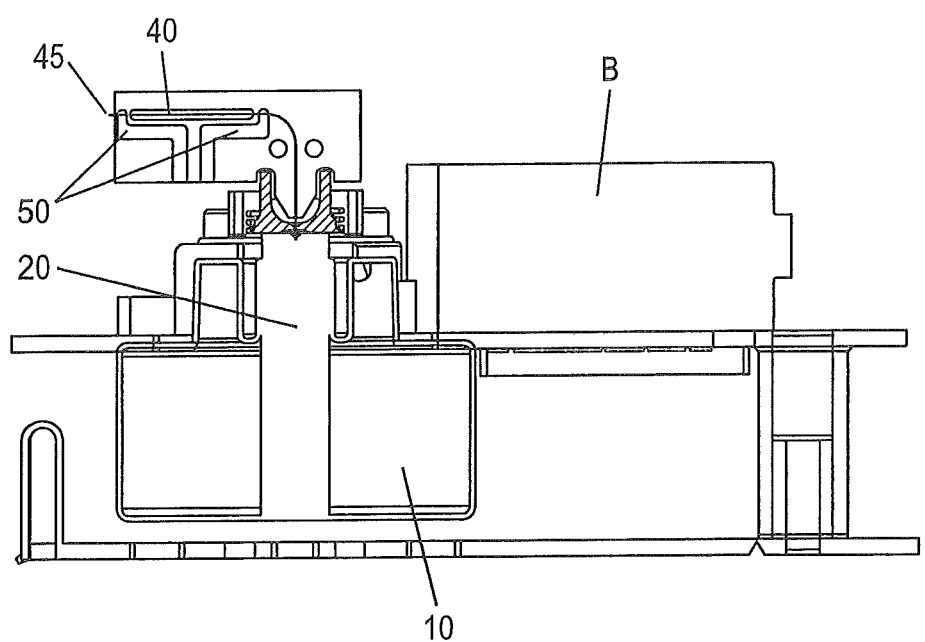

In the preferred embodiment, the capillary passage is designed to have a controlled temperature profile at the outlet end of the capillary passage as described in commonly-owned U.S. Pat. No. 6,640,050 which is incorporated herein by reference in its entirety. In such an embodiment (FIG. 3A), the inlet and outlet electrode 50 have low electrical resistivity and can be made of copper, silver, gold, aluminum and the like. A resistance wire 70 connected in series between the capillary outlet 45 and outlet electrode 50 has an electrical resistance equal to 10% to 30% of the capillary tube 40 (FIG. 3B). When a sufficient voltage is applied between the two electrodes 50, the capillary tube 40 and resistance wire 70 increase in temperature relative to the electrodes 50. With the appropriate ratio of electrical resistances in the capillary tube 40 and resistance wire 70, the temperature of the capillary tube 40 will linearly increase along its length, maximizing at the outlet 45 to provide a controlled temperature profile of the heated capillary tube.

Another consideration in the air freshener design is pressure drop. When the fluid within the capillary tube 40 is volatilized, pressure is created. That pressure can push some of the fluid in the capillary tube 40 back toward the liquid supply 10 reducing overall output. In the preferred embodiment, having a constriction 80 on the inlet end 47 of the capillary tube 40 prior to the heating zone is preferred (FIG. 3B). The restriction 80 is formed to reduce the cross-sectional area of the capillary tube 40 up to 75% (e.g., 25-75%). Optionally, the restriction may be a separate orifice 85 placed between the liquid supply 10 and capillary tube 40 (FIG. 3C).

The output from the air freshener is dependent on the number of capillaries, capillary internal dimensions and frequency of actuation. A potential embodiment could have a number of capillaries in parallel drawing fluid from a common liquid supply or separate liquid supplies (having different fragrances). The control circuitry could actuate each capillary sequentially producing a near continuous aerosol output.

It is desirable for an air freshener, producing an aerosol, for the particle size to be as small as possible. Stokes' Law predicts the settling velocity of small spheres in fluid such as air or water. The equation for Stokes' Law is: $w=2\ (\rho_p-\rho_f)\ gr^2/9\mu$ where w is the settling velocity, $\rho$ is density (the subscripts p and f indicate particle and fluid respectively), g is the acceleration due to gravity, r is the radius of the particle and $\mu$ is the dynamic viscosity of the fluid. The following table indicates the settling velocity in air for a series of particle sizes from 1-50 micron.

| Diameter Micron | Settling Velocity cm/sec |
| --- | --- |
| 1 | 0.003 |
| 5 | 0.07 |
| 10 | 0.3 |
| 50 | 7.4 |

The aerosol particle size produced is preferably less than 5 micron and more preferably from 1-3 microns. This results in particle settling velocities less than 0.07 cm/sec, allowing the aerosol to "hang" in the air for long periods of time, thereby enhancing distribution in the environment and evaporation of the fragrance. Air fresheners using pressurized aerosol cans will typically have an aerosol particle size greater than 20 microns and thus much shorter duration (hang time) of air freshening effect.

In further explanation of the above embodiments and in reference to FIG. 3C, it is to be realized that the region of the capillary tube 40 between electrodes 50 defines a heated portion 90 (heated zone) along the capillary tube 40. Preferably the heated zone terminates adjacent the outlet 45 (tip or discharge end) of the capillary tube 40. At initiation of a power cycle, this heated portion 90 along the capillary tube 40 is already filled with liquid supplied via capillary action from the liquid supply 10. Such capillary feeding may be through the wick 20 or an extension of the capillary tube 40 or a combination of both. During the power cycle, any tendency for liquid to be drawn into the heated zone 90 is interrupted by the volatilization of liquid already within the heated zone 90, and preferably sufficient energy is applied along the heated portion of the capillary tube 40 to fully evacuate the liquid along the heated zone 90 by conclusion of the power cycle. The requisite energy is readily resolved by knowing the volume and therefore the mass of liquid contained along the heated zone 90 of the capillary tube 40, the latent heat of that mass plus the specific heat of the volume/mass, with the addition of approximately 25% margin to accommodate variations and losses. Such operation assures that the liquid is fully evacuated and does not remain at any location along the heated zone 90 of the capillary tube 40, so that feeding of the heated zone 90 via capillary action can resume after completion of the power cycle and is not blocked. The time between power cycles (aerosolization of liquid) is timed apart by a time greater than the time required for capillary action to draw liquid from the liquid supply 10 and refill the heated zone 90.

Advantageously, this system achieves heated capillary aerosol generation without the complications of a mechanical pumping apparatus. Semi-continuous operation may be achieved by operating several capillary passages off of a common liquid supply 10 or separate liquid supplies, and programming a controller to operate one capillary passage after another in repeated sequence, with timing and the number of capillary passages being sufficient for the capillary liquid supplying operations to reach completion between power cycles for a given capillary passage.

The disclosed system is readily adapted to discharging fragrances (air fresheners and the like), insect repellents, insecticides, fumigants, lubricants, pest and weed control agents, and the like. In still air, including indoor applications, the aerosolization system as described herein is particularly advantageous because of the enhanced linger time (hang time) of the aerosol particles and the system's ability to create more plume with less liquid material, due to the small particle size achieved with the disclosed aerosolizer verses previously existing aerosolizers.

While various embodiments have been described, it is to be understood that variations and modifications may be resorted to as will be apparent to those skilled in the art. Such variations and modifications are to be considered within the purview and scope of the claims appended hereto.

What is claimed is:

1. A pulsed aerosol generator comprising:
   a capillary passage having an inlet and an outlet;
   a liquid supply operable to supply liquid material to the inlet of the capillary passage only via capillary action along a supply path of capillary action, said supply path essentially free of heating;
   a power supply adapted to apply voltage across a heater arranged along a heated portion of the capillary passage to heat liquid material in the capillary passage to a temperature sufficient to at least partially volatilize liquid material in the capillary passage such that the liquid material is driven out of the outlet of the capillary passage and forms aerosolized liquid material; and
   wherein the capillary passage comprises an interior of a tube and the capillary passage includes a constriction at a location adjacent the inlet of the capillary tube.

2. The pulsed aerosol generator of claim 1, wherein the liquid supply comprises a wick that delivers the liquid material to the inlet of the capillary passage.

3. The pulsed aerosol generator of claim 2, wherein the wick comprises a porous plastic wick.

4. The pulsed aerosol generator of claim 1, wherein the capillary passage has a reduced diameter at the outlet of the capillary passage.

5. The pulsed aerosol generator of claim 4, wherein the capillary passage has a restricted orifice at the outlet, the restricted orifice having a diameter of about 0.05 mm.

6. The pulsed aerosol generator of claim 5, wherein the capillary passage has an internal diameter of about 0.05 to 0.4 mm and a length of about 10 to 40 mm.

7. The pulsed aerosol generator of claim 1, wherein the power supply includes a supercapacitor that supplies an energy pulse to the heater.

8. The pulsed aerosol generator of claim 1, wherein the capillary passage comprises the interior of a stainless steel tube or the interior of a non-metallic tube.

9. The pulsed aerosol generator of claim 1, further comprising control circuitry operable to deliver power from the power supply to the heater in timed heating cycles such that the liquid material is at least partially volatilized after capillary filling of the capillary passage.

10. The pulsed aerosol generator of claim 1, wherein the constriction reduces a cross-sectional area of the capillary passage at said location by up to 75%.

11. An aerosol generator to generate an aerosolized liquid material comprising:
    a zone operable to be heated, said zone having an inlet and an outlet;
    a liquid supply to supply a liquid material to the inlet of the zone via capillary action along a supply path of capillary action, said supply path essentially free of heating;
    a power supply operable to repetitively apply heat according to a power cycle along at least a portion of the zone to volatilize the liquid material disposed in the heated zone so that during the power cycle, the drawing of liquid via capillary action is interrupted and that at conclusion of each power cycle, the disposed liquid along the zone is evacuated from the heated zone, the power cycles sufficiently spaced apart in time for drawing liquid via capillary action to resume and refill the zone between power cycles; and
    wherein the zone comprises an interior of a tube and the zone includes a constriction at a location adjacent the inlet of the zone.

12. The aerosol generator of claim 11, wherein the power supply includes at least one supercapacitor.

13. The aerosol generator of claim 11, wherein liquid is supplied to the heated zone by a wick and power to the heated zone is controlled by a microcontroller.

14. The pulsed aerosol generator of claim 11, wherein the constriction reduces a cross-sectional area of the zone at said location by up to 75%.

* * * * *